(12) United States Patent
Allouche et al.

(10) Patent No.: US 8,873,033 B1
(45) Date of Patent: Oct. 28, 2014

(54) CURED-IN-PLACE-PIPE LINER INSPECTION SYSTEM AND METHOD

(75) Inventors: Erez Allouche, Madison, MS (US); Shaurav Alam, Ruston, LA (US)

(73) Assignee: Louisiana Tech University Research Foundation a division of Louisiana Tech University Foundation Inc., Ruston, LA (US)

( * ) Notice: Subject to any disclaimer, the term of this patent is extended or adjusted under 35 U.S.C. 154(b) by 560 days.

(21) Appl. No.: 13/289,705

(22) Filed: Nov. 4, 2011

Related U.S. Application Data (60) Provisional application No. 61/410,469, filed on Nov. 5, 2010.

(51) Int. Cl.
 *G01N 21/00* (2006.01)

(52) U.S. Cl.
 USPC .................................. 356/241.1; 356/241.6

(58) Field of Classification Search
 USPC ........................................ 356/241.1–241.5
 See application file for complete search history.

(56) References Cited

U.S. PATENT DOCUMENTS

| | | | |
|---|---|---|---|
| 3,676,269 A * | 7/1972 | Schaetti | 156/548 |
| 4,226,630 A | 10/1980 | Styron | |
| 5,055,694 A * | 10/1991 | Jeffers et al. | 250/458.1 |
| 5,810,920 A | 9/1998 | Ueshima et al. | |
| 5,855,830 A * | 1/1999 | Abe | 264/40.1 |
| 6,632,876 B2 | 10/2003 | Soukatchoff | |
| 7,347,896 B2 | 3/2008 | Harrison | |
| 2003/0232134 A1 * | 12/2003 | Williams et al. | 427/209 |
| 2005/0016418 A1 | 1/2005 | Holbek | |
| 2010/0212803 A1 * | 8/2010 | Carr et al. | 156/60 |
| 2013/0234030 A1 * | 9/2013 | Shelley et al. | 250/353 |

FOREIGN PATENT DOCUMENTS

JP     2000167458 A   *   6/2000

OTHER PUBLICATIONS

S. Alam and E. Allouche, LinerRite—An Optical-Based Sensor for Detecting the Quality of Wet-Out and Curing Operations of CIPP Liners, Trenchless Technology Center Industry Advisory Board Meeting, Ruston, LA (Oct. 20-22, 2010).
LinerRite—Innovative NDT Method for Quality Control of CIPP Liners, Louisiana Tech University Trenchless Technology Center Newsletter, 20-21 (Mar. 2011).
E. Allouche, LinerRite—Next Generation of QC/QA Tools for CIP Liners, Trenchless Technology Center Industry Advisory Board Meeting, Ruston, LA (Oct. 27-28, 2011).
U.S. Appl. No. 12/972,722, "Geopolymer Mortar and Method," Erez Allouche and Carlos Montes, filed Dec. 20, 2010 (co-pending application).

(Continued)

*Primary Examiner* — Hoa Pham
(74) *Attorney, Agent, or Firm* — Jones Walker LLP (57) ABSTRACT

A cured-in-place-pipe (CIPP) liner inspection system used to inspect a resin level in a CIPP liner that has been impregnated with resin using an inspection chamber having an optical sensor. The CIPP liner inspection system is also used to identify zones within an installed CIPP liner having lower mechanical strength due to inadequate distribution of resin using a robotic unit having an optical sensor. The optical sensor measures an optical property, which is used to determine a resin level or a mechanical property based on predetermined correlations between the optical property and the resin level and predetermined correlations between the optical property and the mechanical property.

8 Claims, 12 Drawing Sheets

(56) References Cited

OTHER PUBLICATIONS

U.S. Appl. No. 13/594,164, "Incinerator Fly Ash Geopolymer and Method," Erez Nissim Allouche and Eleazar Ivan Diaz-Loya, filed Aug. 24, 2012 (co-pending application).
U.S. Appl. No. 13/481,494, "Method for Geopolymer Concrete," Erez Nissim Allouche and Eleazar Ivan Diaz-Loya, filed May 25, 2012 (co-pending application).

PCT International Searching Authority/US, International Search Report, mailed Apr. 20, 2012, for PCT/US2011/65854, "Geopolymer Mortar and Method" (related to co-pending application).
PCT International Searching Authority/US, Written Opinion of the International Searching Authority, mailed Apr. 20, 2012, for PCT/US2011/65854, "Geopolymer Mortar and Method" (related to co-pending application).
Yunsheng, Z., Wei, S., Qianli, C., and Lin,C., Synthesis and heavy metal immobilization behaviors of slag based geopolymer, Journal of Hazardous Materials 143, 206-213 (2007).

* cited by examiner

CURED-IN-PLACE-PIPE LINER INSPECTION SYSTEM AND METHOD

CROSS-REFERENCE TO RELATED PATENT APPLICATIONS

This application claims priority to U.S. Provisional Application No. 61/410,469, filed on Nov. 5, 2010, which is incorporated herein by reference.

BACKGROUND

Cured-in-place-pipe (CIPP) lining is a method of renewing aging and deteriorated sewer pipes and storm drains. A resin-impregnated liner is inserted and situated in the host pipe. The liner is then pressed against the wall of the host pipe, and cured by circulating hot water or steam through the liner, or via the utilization of ultraviolet light train. The liner is typically composed of non-woven polyester felt, which is formed into a tubular sleeve and saturated with thermoset resin. The amount and composition of the resin controls the stiffness of the cured liner. Excess resin renders the CIPP liner overly stiff, while an insufficient amount of resin prevents the CIPP liner from meeting the desired mechanical strength and may compromise the air tightness and water tightness of the CIPP liner. Currently, visual inspection and experience are the only manners of controlling the amount of resin per linear foot of the CIPP liner.

SUMMARY OF SELECTED EMBODIMENT OF INVENTION

A system for detecting a resin level in an impregnated CIPP liner including an inspection chamber having a first roller and a second roller disposed through the inspection chamber. The system may also include a rotation system for rotating the first and second rollers. The system may further include an optical sensor for detecting a resin level in an impregnated CIPP liner traveling between the first and second rollers. The optical sensor may be operatively associated with the inspection chamber. The system may further include a transference system for transferring the optical sensor relative to the inspection chamber.

A system for inspecting a CIPP liner after curing within a host pipe including a robotic unit having an optical sensor capable of measuring an optical value. The robotic unit may also include a durometer capable of measuring a hardness value of a CIPP liner. The robotic unit may further include a resin injection module capable of injecting a resin into an area of the CIPP liner. The optical sensor may be rotatably mounted on the robotic unit.

A method of inspecting a CIPP liner including the steps of impregnating a CIPP liner with a resin to form an impregnated CIPP liner, running the impregnated CIPP liner through an inspection chamber, and inspecting a resin level along a length of the impregnated CIPP liner using an optical sensor operatively associated with the inspection chamber. The resin level may be a concentration of a resin at a specific point along the length of the impregnated CIPP liner. The inspection step may further include measuring an optical property along the length of the impregnated CIPP liner using the optical sensor, determining the resin level along the length of the impregnated CIPP liner using the optical property measured and a predetermined correlation between the optical property and the resin level, and comparing the determined resin level along the length of the impregnated CIPP liner with a minimum allowable resin level. The inspection step may further include identifying a resin-deprived area along the length of the impregnated CIPP liner using the optical sensor. The resin-deprived area may have a resin level below the minimum allowable and/or threshold resin level. The method may further include the steps of automatically stopping the movement of the impregnated CIPP liner through the inspection chamber, and alerting a user of the resin-deprived area. The method may further include repairing the resin-deprived area of the impregnated CIPP liner by adding an additional amount of the resin to the resin-deprived area.

In another embodiment, a method of inspecting a CIPP liner may include the steps of deploying a robotic unit into a CIPP liner after curing in a host pipe, and inspecting one or more mechanical properties along a length and a circumference of the CIPP liner using an optical sensor of the robotic unit. The mechanical properties may be hardness, tensile strength, flexural strength, tensile modulus of elasticity, or flexural modulus of elasticity.

The inspecting step may also include measuring an optical property along the length and the circumference of the CIPP liner using the optical sensor of the robotic unit, determining the mechanical property along the length and the circumference of the CIPP liner using the optical property measured and a predetermined correlation between the optical property and the mechanical property, and comparing the determined mechanical property along the length and the circumference of the CIPP liner with an allowable range for the mechanical property. The inspection step may further include identifying a weak area along the CIPP liner with the optical sensor. The mechanical property of the weak area may be outside of the allowable range for the mechanical property. The method may further include measuring the hardness of the weak area of the CIPP liner using a durometer of the robotic unit, re-determining the mechanical property of the weak area of the CIPP liner using the hardness measured and a predetermined correlation between the hardness and the mechanical property, comparing the re-determined mechanical property of the weak area of the CIPP liner with the allowable range for the mechanical property, and repairing the weak area of the CIPP liner if the re-determined mechanical property of the weak area is also outside of the allowable range for the mechanical property.

DETAILED DESCRIPTION OF THE SELECTED EMBODIMENTS

A CIPP liner inspection system may be used to control the quality of the resin impregnation process, also referred to as the wet-out process, of CIPP liners by detecting with optical sensors and monitoring the amount of resin per linear foot of the CIPP liners. The CIPP liner inspection system may also be used to identify with optical sensors zones within an installed CIPP liner having lower mechanical strength due to inadequate distribution of the resin. The CIPP liner inspection system may accomplish these objectives by correlating the centroid of a peak wavelength measured in the nanometer scale visual range with the mechanical properties of an installed CIPP liner.

An incident light may be applied to the CIPP liner surface, and the diffuse reflectance spectrum may be collected by a fiber optic probe and directed to an optical detector. A computer program may record the diffuse reflectance spectrum readings of the optical detector and calculate the centroid of the diffuse reflectance spectrum. The centroid is a function of the color and texture of the CIPP liner surface. Color and texture of well impregnated and cured CIPP liners are even, while that of poorly impregnated or under-cured CIPP liners are not. Poorly impregnated and under-cured CIPP liners have lower hardness, tensile modulus of elasticity, and flexural modulus of elasticity values. Therefore, a relationship exists between the wavelength of the diffuse reflection spectrum and the mechanical properties of the CIPP liner.

The spectral centroid is the "center of mass" of the diffuse reflectance spectrum. The spectral centroid is calculated as the weighted mean of the frequencies in the signal, with the magnitudes serving as the weights as shown in the following equation:

$$\text{Centroid} = \frac{\sum_{n=0}^{N-1} f(n)x(n)}{\sum_{n=0}^{N-1} x(n)}$$

where $x(n)$ represents the magnitude of bin number n, and $f(n)$ represents the center frequency of that bin.

Standard tests are used to measure the mechanical properties of CIPP liners. One such standard test is ASTM D2240, the standard test for measuring the hardness of rubber materials. In this test, a Shore Hardness Type D indenter is used to detect a penetration depth and return a durometer reading, which is a dimensionless quantity. Another standard test is ASTM D638, the standard test for measuring the tensile properties of plastic materials by elongating a specimen and measuring the load carrying capacity of the specimen. A stress-strain curve can be plotted for the material using the specimen's dimensions, load, and deflection. Tensile modulus of elasticity is the slope of the elastic region of a stress-strain curve produced by ASTM D638. A third standard test is ASTM D790, the standard test for measuring the flexural properties of plastics and electrical insulating materials by subjecting a specimen to three-point loading. The flexural strength is the maximum applied load recorded during the test. Flexural modulus of elasticity is the slope of the elastic region of a stress-strain curve produced by ASTM D790.

In an experiment, three commercially available resins from two vendors were tested, namely, Resin A, Resin B, and Resin C. Resin A was QUIKPDX, an epoxy-based resin available through Pipelining Supply Inc. of Anaheim, Calif. Resin B was CORVE8190, a vinyl ester resin available through Pipelining Supply Inc. of Anaheim, Calif. Resin C was Reichhold 33420-75, a polyester resin available through Reichhold Chemicals Inc. of Durham, N.C. Five-inch square felt panels, each having a thickness of one-quarter inch, were used as the CIPP liner samples. The CIPP liner samples were impregnated with different resin levels from 0.5 lb/ft to 3.0 lb/ft at increments of 0.5 lb/ft. The amount of resin added to each CIPP liner sample was calculated based on the designated test resin level, a felt tube having a length of one foot, a diameter of 7.85 inches, and a thickness of 0.275 inches. Table 1 displays the calculations associated with the amount of resin added to each CIPP liner sample, which were labeled T1, T2, T3, T4, T5, T6, and T7.

TABLE 1

| Specimen Designation | Resin lb/ft | Resin lb/in | Resin lb/in$^3$ | Resin gm | Felt gm | Felt + Resin gm |
|---|---|---|---|---|---|---|
| T1 | 0.00 | 0.000 | 0.0000 | 0.0 | 14.6 | 14.6 |
| T2 | 0.50 | 0.042 | 0.0062 | 17.7 | 15.3 | 33.0 |
| T3 | 1.00 | 0.084 | 0.0125 | 35.3 | 15.4 | 50.7 |
| T4 | 1.50 | 0.127 | 0.0187 | 53.0 | 14.0 | 67.0 |
| T5 | 2.00 | 0.167 | 0.0249 | 70.5 | 14.5 | 85.0 |
| T6 | 2.50 | 0.211 | 0.0311 | 88.2 | 13.5 | 101.7 |
| T7 | 3.00 | 0.253 | 0.0374 | 105.9 | 12.9 | 118.8 |

A roller was used to impregnate the resin into the CIPP liner samples. The CIPP liner samples were cured at ambient temperature. Portions of each CIPP liner sample were cut to dimensions as per ASTM D638 and ASTM D790. Based on experimental measurements, tensile and flexural moduli of elasticity were calculated for each specimen. Separate portions of each CIPP liner sample were cut for a spectral test and a hardness test.

Figure 1:
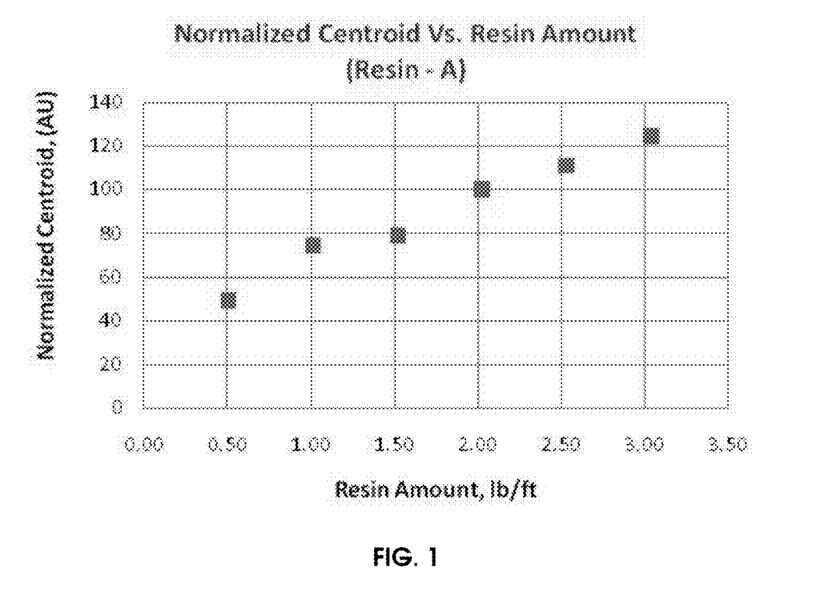
FIG. 1 is a graphical representation of the relationship between experimental results for the normalized centroid and experimental results for the resin amount for Resin A.
Figure 2:
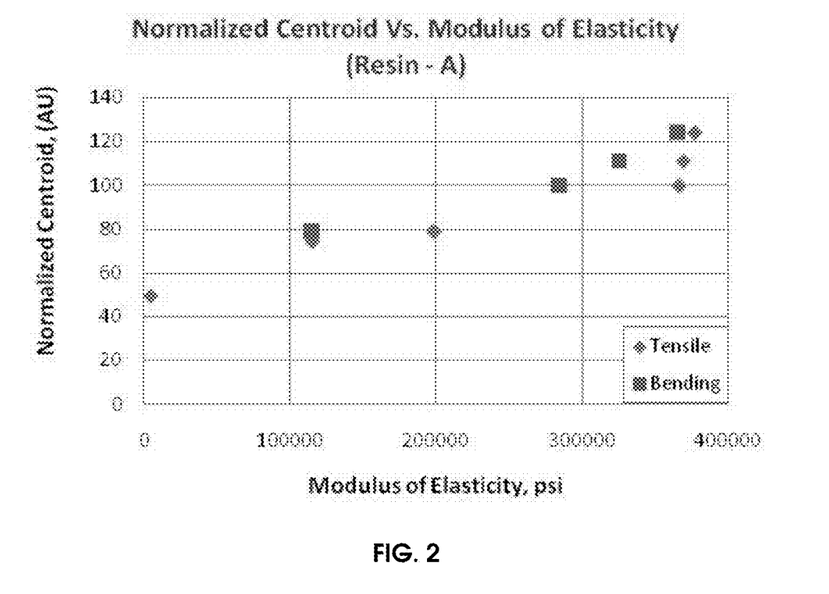
FIG. 2 is a graphical representation of the relationship between experimental results for the normalized centroid and experimental results for the modulus of elasticity for Resin A.
Figure 3:
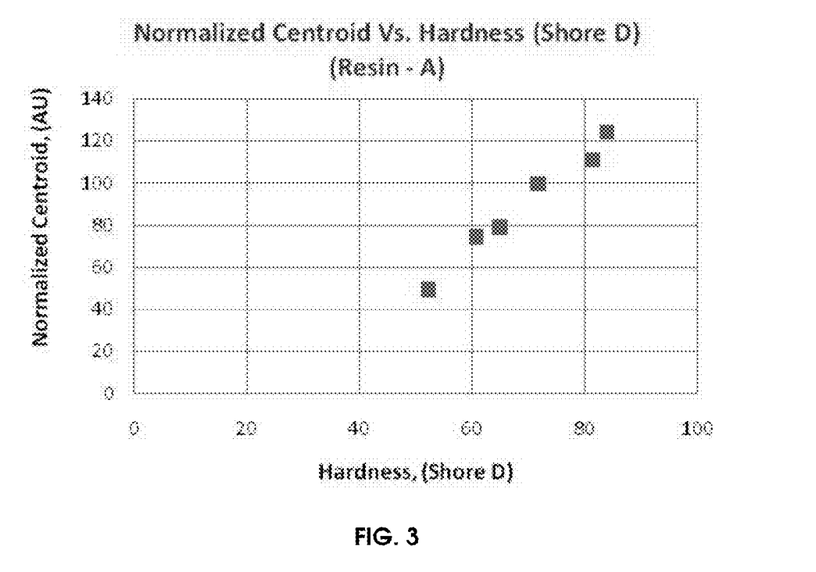
FIG. 3 is a graphical representation of the relationship between experimental results for the normalized centroid and experimental results for the hardness for Resin A.
Figure 4:
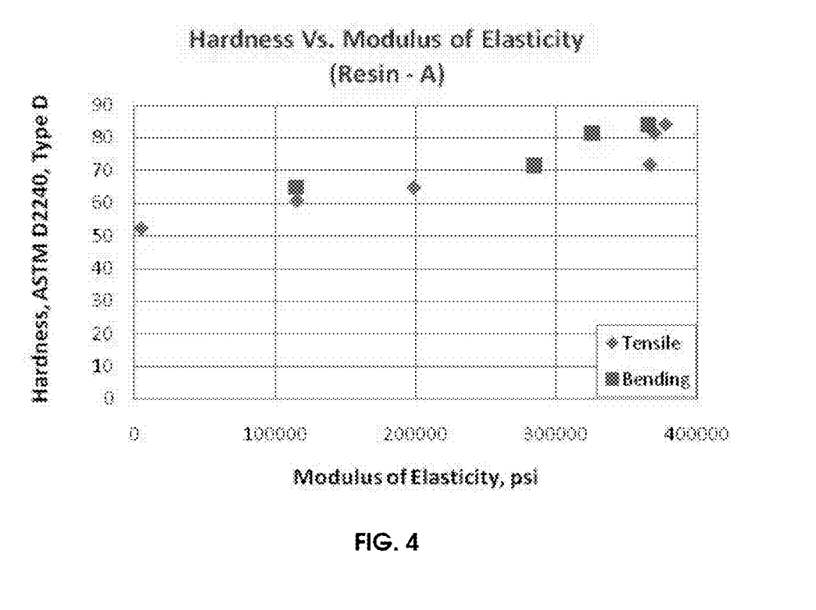
FIG. 4 is a graphical representation of the relationship between experimental results for the hardness and experimental results for the modulus of elasticity for Resin A.
Figure 5:
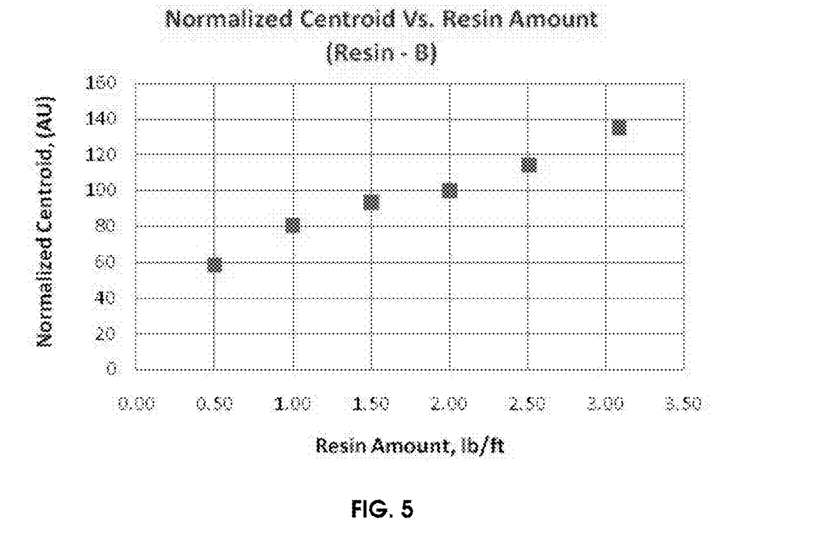
FIG. 5 is a graphical representation of the relationship between experimental results for the normalized centroid and experimental results for the resin amount for Resin B.
Figure 6:
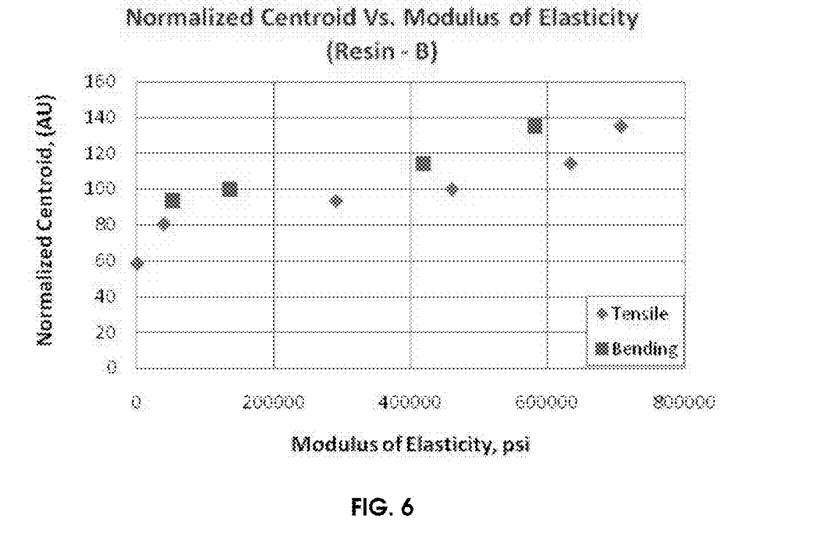
FIG. 6 is a graphical representation of the relationship between experimental results for the normalized centroid and experimental results for the modulus of elasticity for Resin B.
Figure 7:
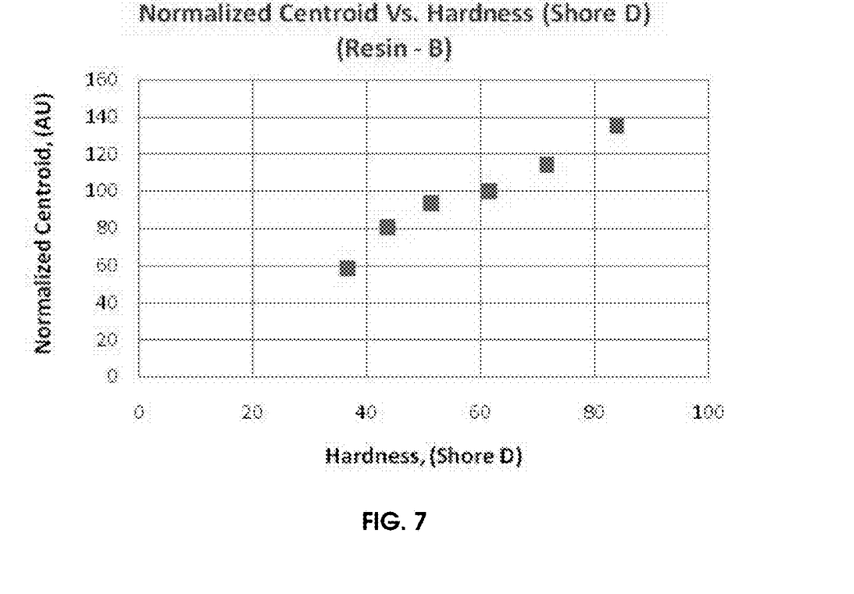
FIG. 7 is a graphical representation of the relationship between experimental results for the normalized centroid and experimental results for the hardness for Resin B.
Figure 8:
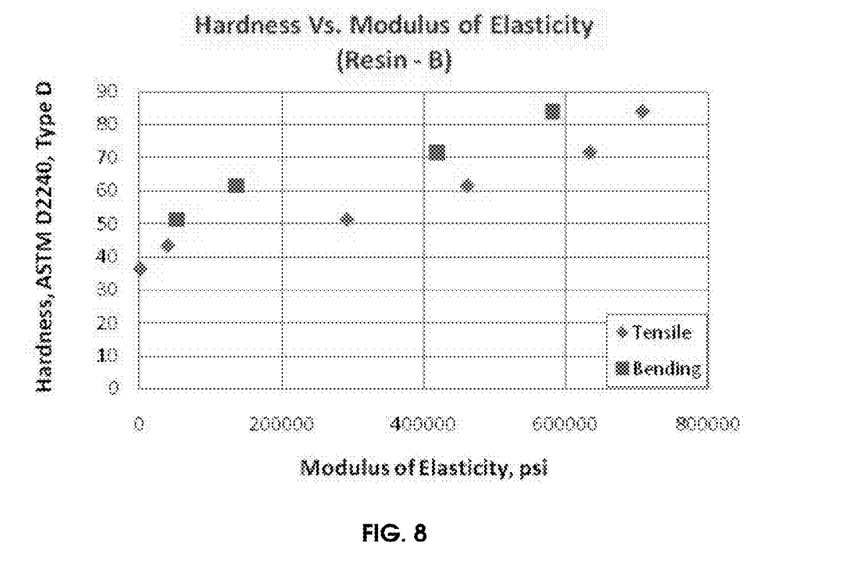
FIG. 8 is a graphical representation of the relationship between experimental results for the hardness and experimental results for the modulus of elasticity for Resin B.
Figure 9:
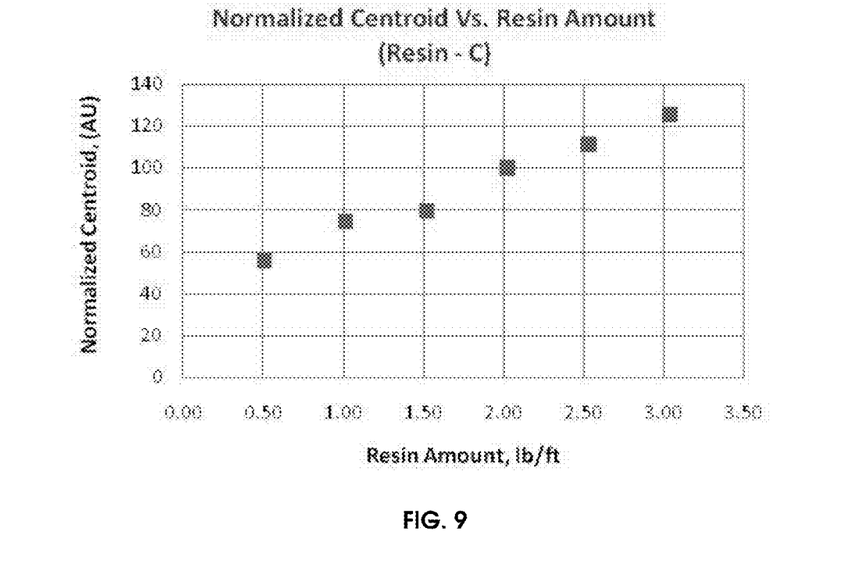
FIG. 9 is a graphical representation of the relationship between experimental results for the normalized centroid and experimental results for the resin amount for Resin C.
Figure 10:
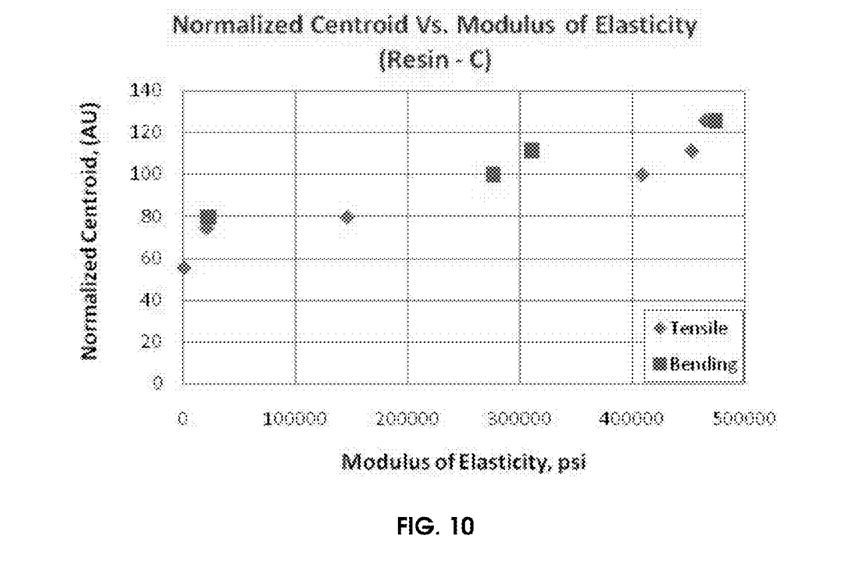
FIG. 10 is a graphical representation of the relationship between experimental results for the normalized centroid and experimental results for the modulus of elasticity for Resin C.
Figure 11:
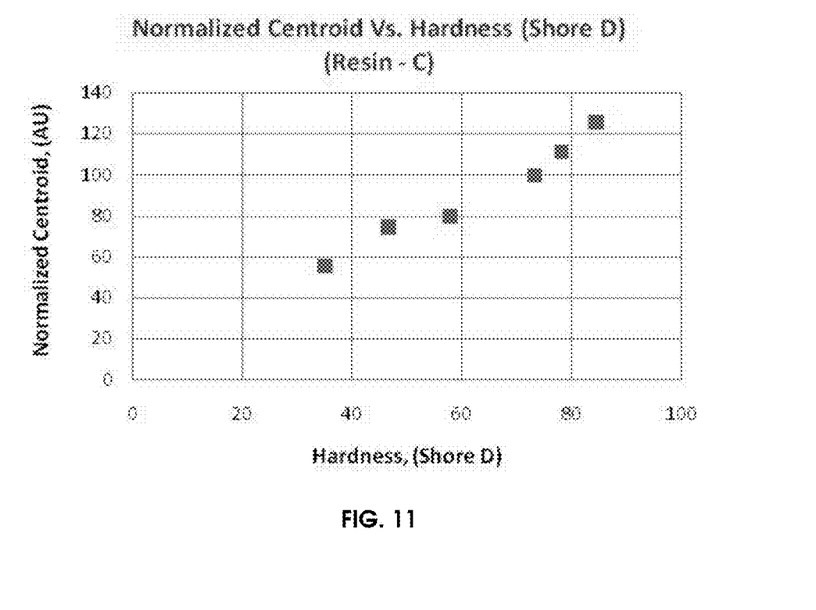
FIG. 11 is a graphical representation of the relationship between experimental results for the normalized centroid and experimental results for the hardness for Resin C.
Figure 12:
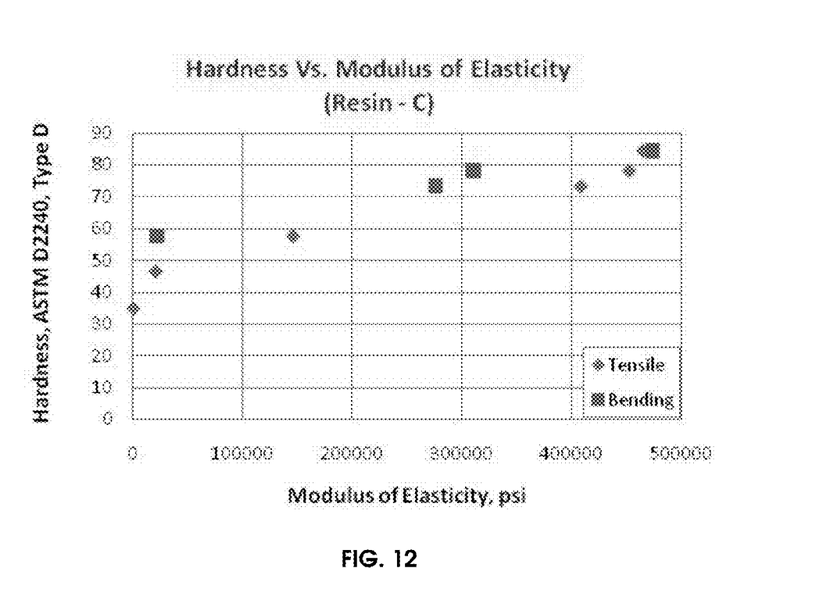
FIG. 12 is a graphical representation of the relationship between experimental results for the hardness and experimental results for the modulus of elasticity for Resin C.

For each CIPP liner sample (T1-T7), average values were calculated from the multiple measurements performed for each property, namely, tensile properties, flexural properties, spectral properties, and hardness. FIGS. 1-3 illustrate the relationships between spectral normalized centroid and resin level, tensile modulus of elasticity, flexural modulus of elasticity (also known as bending modulus of elasticity), and hardness for CIPP liner samples impregnated with Resin A. FIG. 4 illustrates the relationship between hardness and the tensile modulus of elasticity and flexural modulus of elasticity for CIPP liner samples impregnated with Resin A. FIGS. 5-7 illustrate the relationships between the spectral normalized centroid and resin level, tensile modulus of elasticity, flexural modulus of elasticity, and hardness for CIPP liner samples impregnated with Resin B. FIG. 8 illustrates the relationship between hardness and the tensile modulus of elasticity and flexural modulus of elasticity for CIPP liner samples impregnated with Resin B. FIGS. 9-11 illustrate the relationships between spectral normalized centroid and resin level, tensile modulus of elasticity, flexural modulus of elasticity, and hardness for CIPP liner samples impregnated with Resin C. FIG. 12 illustrates the relationship between hardness and the tensile modulus of elasticity and flexural modulus of elasticity for CIPP liner samples impregnated with Resin C. The measured centroid value was normalized by assuming that the centroid value for resin impregnation level of 2 lb/ft is equal to 100. A natural logarithmic relationship exists between spectral normalized centroid values and resin amount, hardness, tensile modulus of elasticity, and flexural modulus of elasticity.

Regression equations were developed for the relationship between the spectral centroid values and the tensile modulus of elasticity and the flexural modulus of elasticity for Resin A, Resin B, and Resin C. Table 2 displays the regression equations where y is the tensile or flexural modulus of elasticity and x is the centroid value. Regression equations were also developed for the relationship between the hardness values and the tensile modulus of elasticity and the flexural modulus of elasticity for Resin A, Resin B, and Resin C. Table 3 displays the regression equations where y is the tensile or flexural modulus of elasticity and x is the hardness value.

TABLE 2

| Resin Type | Flexural Modulus of Elasticity | Tensile Modulus of Elasticity |
| --- | --- | --- |
| Resin A | $y = 34.09 \ln(x) - 319.96$ | $y = 13.719 \ln(x) - 71.947$ |
| Resin B | $y = 15.419 \ln(x) - 77.872$ | $y = 9.2232 \ln(x) - 10.592$ |
| Resin C | $y = 12.776 \ln(x) - 49.891$ | $y = 9.5209 \ln(x) - 16.522$ |

TABLE 3

| Resin Type | Flexural Modulus of Elasticity | Tensile Modulus of Elasticity |
| --- | --- | --- |
| Resin A | $y = 15.024 \ln(x) - 111.2$ | $y = 5.9211 \ln(x) - 0.6515$ |
| Resin B | $y = 12.329 \ln(x) - 83.609$ | $y = 5.7359 \ln(x) - 8.7716$ |
| Resin C | $y = 7.9255 \ln(x) - 22.099$ | $y = 7.5285 \ln(x) - 22.54$ |

A software program was developed for the CIPP liner inspection system. The software program may directly read the spectral centroid. A database may store the spectral centroid, hardness, tensile modulus of elasticity, and flexural modulus of elasticity values for different resin types. The software program may also graphically represent the relationships among these properties.

FIGS. 13-17 illustrate one embodiment of the CIPP liner inspection system that may be used during the wet-out process. Inspection chamber 10 may include top surface 12, first vertical support 14, and second vertical support 16. First roller 18 and second roller 20 may extend through inspection chamber 10. First roller 18 may extend through first apertures 22 in first and second vertical supports 14 and 16. Second roller 20 may extend through second apertures 24 in first and second vertical supports 14 and 16.

Rotation system 26 may rotate first roller 18 and second roller 20 in opposite directions in order to pull CIPP liner 28 through inspection chamber 10. Rotation system 26 may include first gears 30 and second gears 32. First gears 30 may be connected to each end of first roller 18, and second gears 32 may be connected to each end of second roller 20. First and second gears 30 and 32 may be positioned on the exterior of inspection chamber 10. Alternatively, first and second gears 30 and 32 may be positioned within inspection chamber 10. Rotation system 26 may also include electrical motor 34 for rotating first and second gears 30 and 32, such that first and second rollers 18 and 20 are rotated in opposite directions. Electrical motor 34 may be a servo controlled motor that includes an encoder for tracking the rotation of electrical motor 34. The encoder may provide data to software program 36 in order to track the length of CIPP liner 28 that has traveled through first and second rollers 18 and 20. In some embodiments, other types of electrical motors may be used with a separate encoder. Computer 37 may house software program 36 and database 38. In an alternate embodiment, inspection chamber 10 may be completely enclosed with an entrance space and an exit space for CIPP liner 28. Based on the information provided by the encoder, the position of optical sensor 40 and the correlation between the spectral centroid and the resin level, software program 36 may plot a two-dimensional or three-dimensional plot showing the resin concentration as a function of the position within the liner, which may serve as a quality control reporting tool of the wet-out process.

Figure 13:
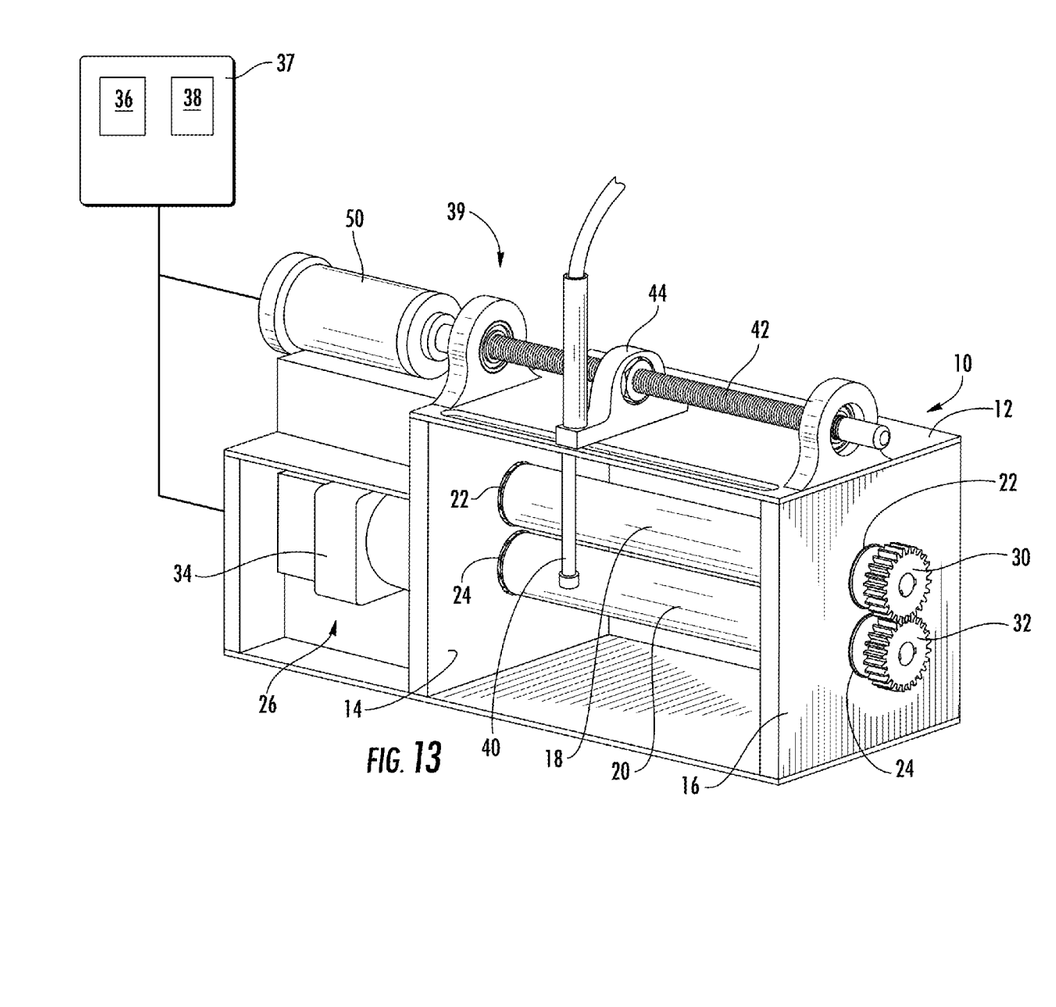
FIG. 13 is a perspective view of an inspection chamber in one embodiment of an inspection system for CIPP liners.
Figure 14:
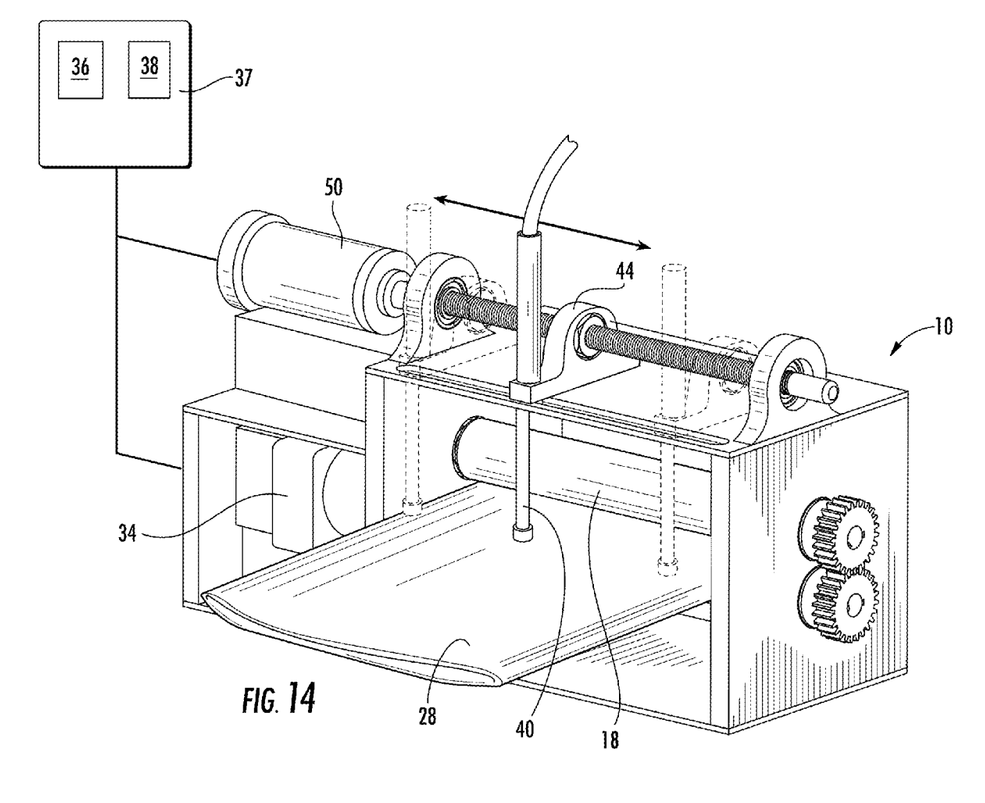
FIG. 14 is another perspective view of the inspection chamber.
Figure 15:
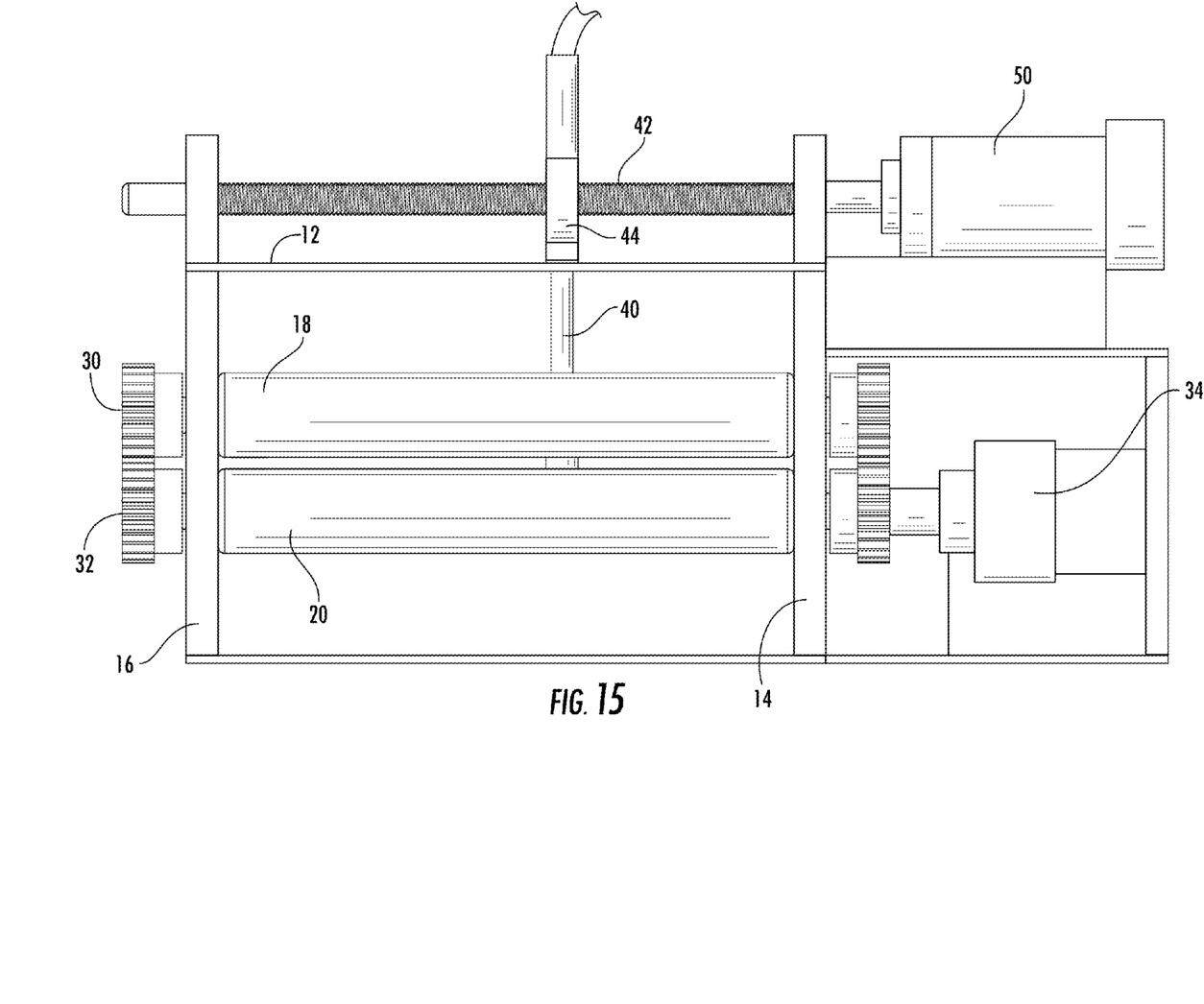
FIG. 15 is a rear view of the inspection chamber.
Figure 16:
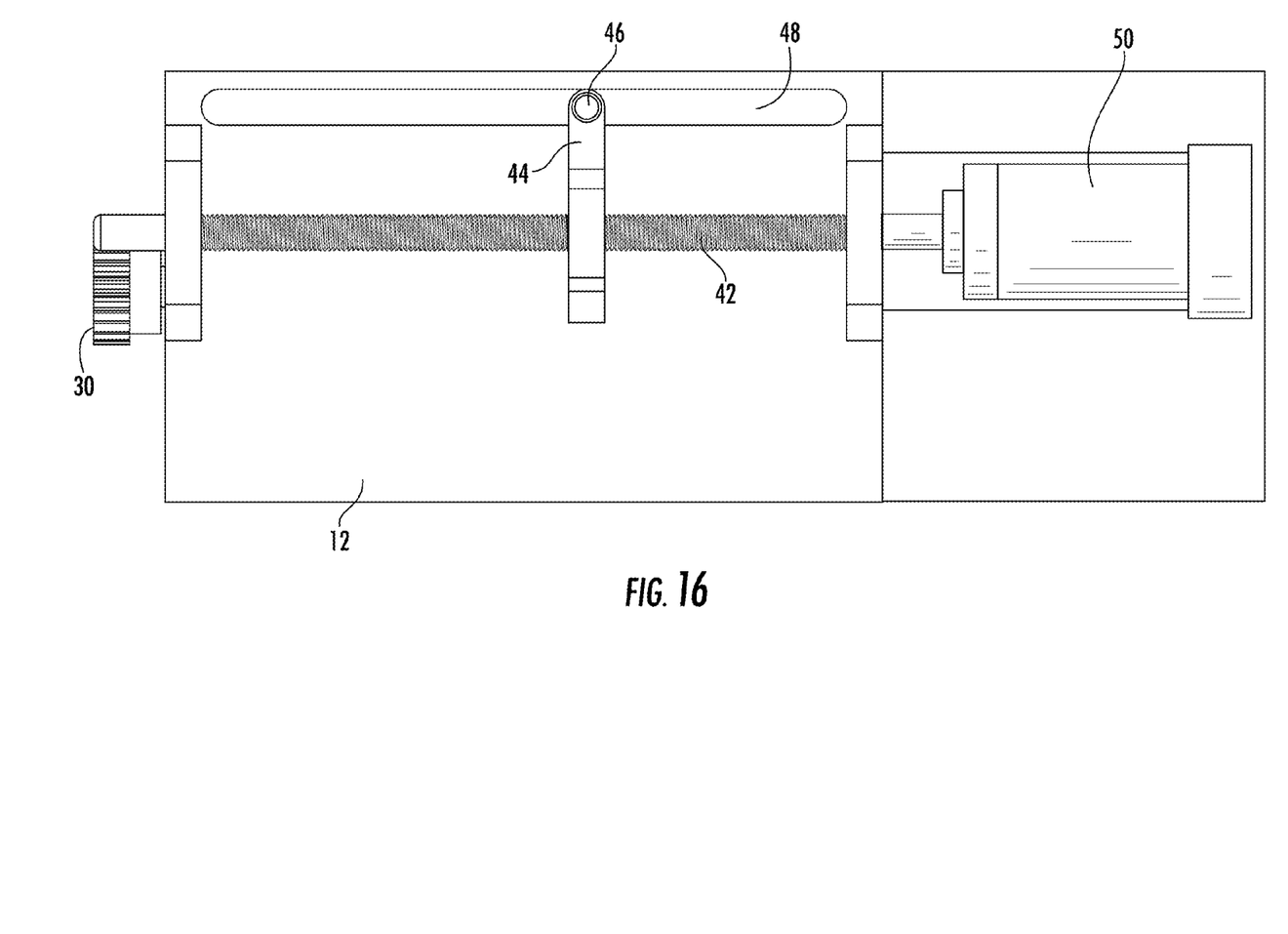
FIG. 16 is a top view of the inspection chamber.
Figure 17:
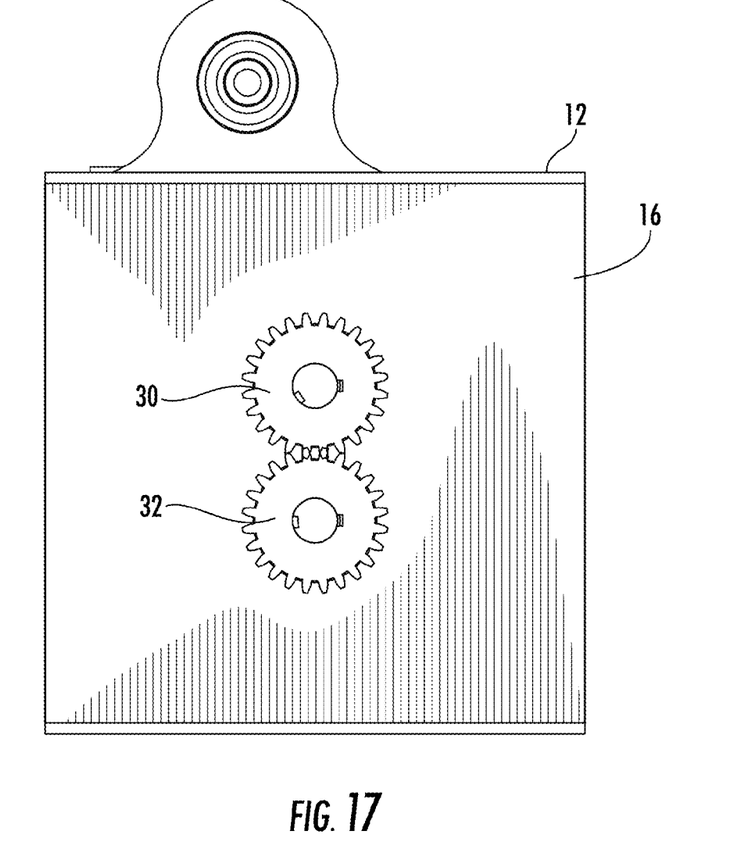
FIG. 17 is a side view of the inspection chamber.

Transference system 39 may be used to transfer optical sensor 40 longitudinally along inspection chamber 10 for detecting a resin level at various positions across the width of CIPP liner 28 as it travels through first and second rollers 18 and 20. Transference system 39 may include transference rod 42 and guide 44 disposed above top surface 12. Transference rod 42 may be threaded, and guide 44 may be threadedly connected to transference rod 42. During use, optical sensor 40 may be disposed through aperture 46 of guide 44 and longitudinal aperture 48 in top surface 12. Transference system 39 may also include electrical motor 50 for rotating transference rod 42, thereby moving guide 44 longitudinally along inspection chamber 10 and moving optical sensor 40 longitudinally within longitudinal aperture 48. Electrical motor 50 may be a servo controlled motor. In an alternate embodiment, inspection chamber 10 may include two or more optical sensors 40. For example, inspection chamber 10 may include one optical sensor 40 positioned as shown in FIG. 13 for detecting the resin level of the top of CIPP liner 28 and another optical sensor 40 positioned below the path of CIPP liner 28 for detecting the resin level of the bottom of CIPP liner 28.

In one embodiment, inspection chamber 10 may have a length of 10 inches, a width of 6 inches, and a height of 6 inches. First and second rollers 18 and 20 may each have a diameter of 1.32 inches. First and second rollers 18 and 20 may be spaced 0.18 inches apart, depending upon the amount of resin impregnated into CIPP liner 28. First and second gears 30 and 32 may be 14.5 degree spur gears each having 0.5-inch steel finished bores, 16 pitch, 24 teeth, and 1.5 inch pitch diameter. When attached to the ends of first and second rollers 18 and 20, each of first and second gears 30 and 32 may extend 1 inch beyond first vertical support 14 and second vertical support 16. The center of first gears 30 may be positioned 2.25 inches below top surface 12 on first and second vertical supports 14 and 16. The center of second gears 32 may be positioned 2.25 inches above the bottom of first and second vertical supports 14 and 16. The center of first gear 30 and the center of second gear 32 may be positioned 1.5 inches apart on first vertical support 14. The center of first gear 30 and the center of second gear 32 may be positioned 1.5 inches apart on second vertical support 16. Transference rod 42 may have a diameter of 0.5 inches, and its center may be positioned 1 inch above top surface 12. Longitudinal aperture 48 may be 0.25 inches from the front of top surface 12. Longitudinal aperture 48 may begin 0.5 inches from first vertical support 14 and end 0.5 inches from second vertical support 16 on top surface 12. Longitudinal aperture 48 may have a width of 0.5 inches and a length of 9 inches.

After impregnating CIPP liner 28 with a resin, CIPP liner 28 may be drawn through the space between first and second rollers 18 and 20 by the rotation of first and second rollers 18 and 20 facilitated by first gears 30, second gears 32, and electrical motor 34. As CIPP liner 28 exits first and second rollers 18 and 20, optical sensor 40 is moved along the width of CIPP liner 28 by transference system 39 in order to measure an optical property along the length of CIPP liner 28. The resin level at the point of measurement on CIPP liner 28 is determined using the optical property measured by optical sensor 40 and a predetermined correlation between the optical property and the resin level. For example, the optical property may be a wavelength, and the optical sensor may send a signal indicating the wavelength to software program 36. Software program 36 may calculate the spectral centroid of the wavelength peak spectrum. If the spectral centroid is less than a predetermined percentage or value, software program 36 may warn a user of a possible problem through audio or visual indication, text, or any other type of notification.

Software program 36 may also determine the resin level using the spectral centroid and a predetermined correlation between the spectral centroid and the resin level. In one embodiment, the predetermined correlation may be a regression equation derived from FIG. 1, 5, or 9. Software program 36 may compare the determined resin level with a minimum allowable resin level. If the resin level is lower than a minimum allowable resin level, software program 36 may automatically stop electrical motor 34, thereby stopping the movement of CIPP liner 28 through first and second rollers 18 and 20. Software program 36 may also alert a user to the resin-deprived area through audio or visual indication, text, or any other type of notification. A user may repair the resin-deprived area of CIPP liner 28 by adding additional resin to the resin-deprived area. Alternatively, the addition of resin to a resin-deprived area may be automated and initiated by software program 36. Additionally, database 38 associated with software program 36 may record the location of the resin-deprived area through the timing of the alert and the data received from the encoder of electrical motor 34. In this way, inspection chamber 10 inspects the resin level in impregnated CIPP liner 28.

In one embodiment, first and second rollers 18 and 20 pull CIPP liner 28 through inspection chamber 10 in order to monitor the resin level in CIPP liner 28 that is already impregnated with resin. CIPP liner 28 may be impregnated with the resin by forcing CIPP liner 28 through a set of calibration rollers, which control the amount of resin impregnated into CIPP liner 28 per unit length. The set of calibration rollers may be rotated by an electrical motor and gear box in order to move CIPP liner 28, or the set of calibration rollers may simply rotate freely as first and second rollers 18 and 20 pull CIPP liner 28 through the set of calibration rollers and through inspection chamber 10.

Alternatively, CIPP liner 28 may be impregnated with the resin by forcing CIPP liner 28 through two sets of calibration rollers. The first set of calibration rollers may control the amount of resin impregnated into CIPP liner 28 per unit length, and the second set of calibration rollers may spread the resin within CIPP liner 28. The two sets of calibration rollers may each be rotated by a separate electrical motor and gear box, or the first set of calibration rollers may rotate freely while the second set of calibration rollers is rotated by an electrical motor and gear box to pull CIPP liner 28 through the first and second sets of calibration rollers. Also, the first and second sets of calibration rollers may each rotate freely as first and second rollers 18 and 20 pull CIPP liner 28 through both sets of calibration rollers and inspection chamber 10.

In an alternate embodiment, CIPP liner 28 may be impregnated with resin when it is pulled through first and second rollers 18 and 20 of inspection chamber 10. In this embodiment, first and second rollers 18 and 20 control the amount of resin impregnated into CIPP liner 28 per unit length immediately before the resin level is inspected by optical sensor 40.

Figure 18:
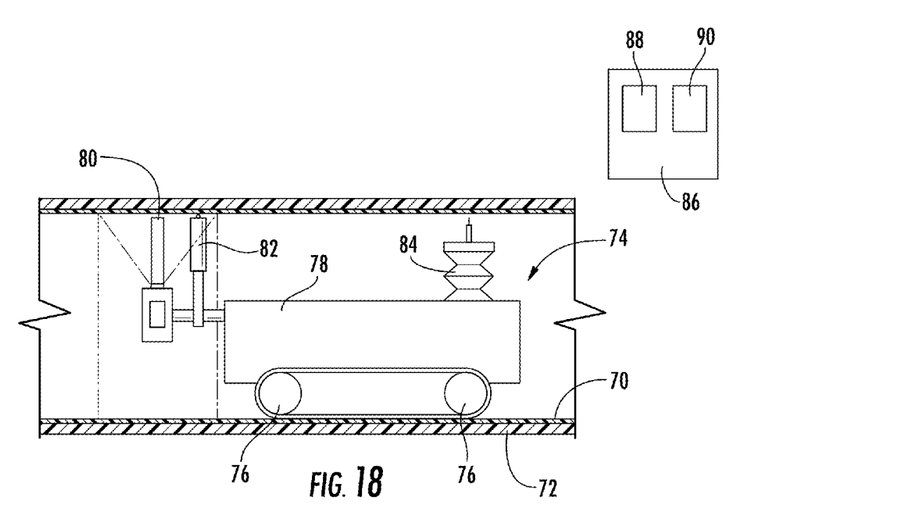
FIG. 18 is a side view of a robotic unit in another embodiment of an inspection system for CIPP liners.
Figure 19:
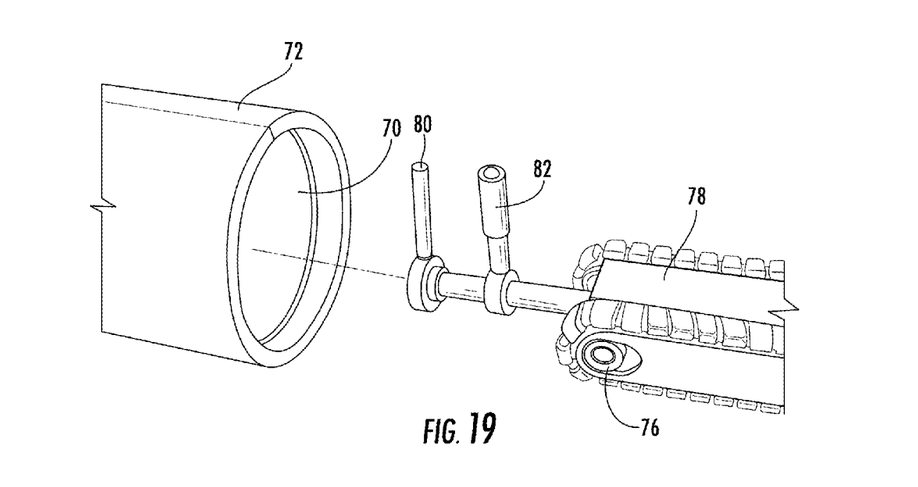
FIG. 19 is a partial perspective view of the robotic unit positioned at an entrance to the CIPP liner.

FIGS. 18-19 illustrate an embodiment of the CIPP liner inspection system that may be used to inspect an installed CIPP liner. CIPP liner 70 may be installed in host pipe 72 and cured by circulating hot water or steam through CIPP liner 70. Robotic unit 74 may be deployed into installed CIPP liner 70 to inspect one or more mechanical properties of CIPP liner 70. Robotic unit 74 may include rollers 76 and body 78. Optical sensor 80 may be rotatably mounted on body 78 of robotic unit 74 for measuring an optical property of CIPP liner 70 as robotic unit 74 is deployed into CIPP liner 70. Through its rotation, optical sensor 80 may measure the optical property of the interior circumference of CIPP liner 70. Durometer 82 may also be rotatably mounted on body 78 of robotic unit 74 for measuring the hardness of CIPP liner 70 at targeted locations as identified by the optical property measured by optical sensor 80. The rotation of optical sensor 80 and durometer 82 may be controlled by an electrical motor, or another mechanism for controlling rotational movement, mounted on body 78. Alternatively, durometer 82 and optical sensor 80 may also be fixed in a particular rotational orientation on body 78 of robotic unit 74. Resin injection module 84 may also be mounted on body 78 of robotic unit 74 for injecting an additional amount of resin into CIPP liner 70 at a weak area as identified by the optical property measured by optical sensor 80 and the hardness measured by durometer 82. Computer 86 may be electronically connected to robotic unit 74. The electronic connection may be by wire or cable, or through wireless connection. Software program 88 and database 90 may be housed on computer 86.

Robotic unit 74 may be deployed into CIPP liner 70. Optical sensor 80 may measure an optical property along the internal length and circumference of CIPP liner 70. The optical sensor 80 may send a signal to software program 88 indicating the optical property measurement. Software program 88 may determine one or more mechanical properties of CIPP liner 70 using the measured optical property and a predetermined correlation between the optical property and the one or more mechanical properties. The mechanical properties may be hardness, tensile strength, flexural strength, tensile modulus of elasticity, or flexural modulus of elasticity. For example, the optical property may be a wavelength, and optical sensor 80 may send a signal indicating the wavelength to software program 88. Software program 88 may calculate the spectral centroid of the wavelength peak spectrum. If the spectral centroid is less than a predetermined percentage or value, software program 88 may warn a user of a possible problem through audio or visual indication, text, or any other type of notification.

Software program 88 may determine the one or more mechanical properties using the spectral centroid and a predetermined correlation between the spectral centroid and each of the mechanical properties. The predetermined correlation may be a regression equation such as those shown in Table 2. Software program 88 may compare the determined mechanical properties with an allowable range for the mechanical properties. If the mechanical properties are outside of the allowable range, software program 88 may automatically stop robotic unit 74. The area having mechanical properties outside of the allowable range may be considered a weak area. Software program 88 may also alert a user to the weak area through audio or visual indication, text, or any other type of notification.

Software program 88 may then activate durometer 82 to measure the hardness of CIPP liner 70 in the weak area of CIPP liner 70 or any other area of CIPP liner 70 where a hardness measurement is desired. Durometer 82 may also send an electronic signal to software program 88 indicating the hardness value of CIPP liner 70 in the weak area, and software program 88 may re-determine the mechanical properties of the weak area of CIPP liner 70 using the hardness value and a predetermined correlation between the hardness value and each of the mechanical properties. The predetermined correlation may be a regression equation such as those shown in Table 3. Software program 88 may compare the re-determined mechanical properties to the allowable ranges. Alternatively, software program 88 may use data from both optical sensor 80 and durometer 82, separately or cross-correlated, to predict the mechanical properties of CIPP liner 70.

If the re-determined mechanical properties are also outside of the allowable ranges, software program 88 may activate resin injection module 84 to begin repairing the weak area of CIPP liner 70. To repair the weak area of CIPP liner 70, resin injection module 84 may apply an additional amount of resin to the weak area. The additional resin may be cured in the weak area, and the optical property of the cured resin in the weak area may again be measured using optical sensor 80 of robotic unit 74. In this way, robotic unit 74 may be used to inspect one or more mechanical properties of CIPP liner 70 installed within host pipe 72 using optical sensor 80 and/or durometer 82.

The embodiments shown in the drawings and described above are exemplary of numerous embodiments that may be made within the scope of the appended claims. It is contemplated that numerous other configurations may be used, and the material of each component may be selected from numerous materials other than those specifically disclosed. In short, it is the applicant's intention that the scope of the patent issuing herefrom will be limited only by the scope of the appended claims.

The invention claimed is:

1. A system for detecting a resin level in an impregnated cured-in-place-pipe (CIPP) liner, comprising:
   an inspection chamber comprising a top surface supported by a first vertical support and a second vertical support;
   a first roller and a second roller disposed through said inspection chamber and supported by said first vertical support and said second vertical support;
   a rotation system for rotating said first roller and said second roller;
   an optical sensor for detecting a resin level in an impregnated CIPP liner traveling between said first roller and said second roller, said optical sensor operatively associated with said inspection chamber; and
   a transference system for transferring said optical sensor relative to said inspection chamber.

2. The system of claim 1, wherein said first roller extends through a first aperture in said first vertical support and a first aperture in said second vertical support, and wherein said second roller extends through a second aperture in said first vertical support and a second aperture in said second vertical support.

3. The system of claim 1, wherein said optical sensor is disposed within said inspection chamber.

4. The system of claim 1, wherein said first roller is disposed above said second roller.

5. The system of claim 1, wherein said rotation system comprises:
   a pair of first gears each operatively connected to an end of said first roller;
   a pair of second gears each operatively connected to an end of said second roller; and
   an electrical motor operatively connected to said first gears and said second gears for rotating said first gears and said second gears in opposite directions such that said first roller and said second roller are rotated in opposite directions.

6. The system of claim 5, wherein the opposite rotation of said first roller and said second roller pushes said CIPP liner forward through said first roller and said second roller.

7. The system of claim 1, wherein said transference system comprises:
   a transference rod disposed above said top surface of said inspection chamber;
   a guide threadedly attached to said transference rod, said guide comprising an aperture dimensioned to receive said optical sensor;
   a longitudinal aperture in said top surface dimensioned to receive said optical sensor; and
   an electrical motor operatively connected to said transference rod, wherein said electrical motor rotates said transference rod for transferring said guide and said optical sensor along said inspection chamber.

8. The system of claim 7, further comprising: a computer electronically connected to said optical sensor, wherein said computer comprises a software program for reading an optical measurement of said optical sensor and correlating said optical measurement of said optical sensor with a resin level of said CIPP liner, and wherein said computer further comprises a database for storing a set of known values for said optical measurement and said resin level.

\* \* \* \* \*